United States Patent [19]

Wootan

[11] Patent Number: 4,742,821
[45] Date of Patent: May 10, 1988

[54] PATIENT RESTRAINT APPARATUS

[76] Inventor: Gerald D. Wootan, 1532 Skyline Circle, Sapulpa, Okla. 74066

[21] Appl. No.: 823,688

[22] Filed: Jan. 29, 1986

[51] Int. Cl.⁴ .............................................. A61F 5/37
[52] U.S. Cl. .................................................... 128/134
[58] Field of Search ................... 128/87 R, 133, 134, 128/135; 269/322, 328

[56] References Cited

U.S. PATENT DOCUMENTS

| | | | |
|---|---|---|---|
| 648,621 | 5/1900 | Hooper | 128/134 |
| 892,047 | 6/1908 | Halterman | 128/134 |
| 919,159 | 4/1909 | Goddard | 5/494 |
| 2,664,083 | 12/1953 | Heymans | 128/134 |
| 2,722,694 | 11/1955 | Bryant | 128/134 |
| 2,927,581 | 3/1960 | Queen | 128/134 |
| 2,940,443 | 6/1960 | Baker | 128/134 |
| 2,948,278 | 8/1960 | Topa | 128/134 |
| 3,093,132 | 6/1963 | Bailey | 128/134 |
| 3,361,132 | 1/1968 | Rentsch, Jr. | 128/134 |
| 3,399,670 | 9/1968 | Veasey | 128/134 |
| 3,407,807 | 10/1968 | Giberson | 128/134 |
| 4,601,075 | 7/1986 | Smith | 128/134 X |

FOREIGN PATENT DOCUMENTS 165043 12/1985 European Pat. Off. .......... 128/87 R

OTHER PUBLICATIONS

Posey Catalog dated Jul. 1, 1972, published By Posey Company, Pasadena, CA. 91107.

Primary Examiner—Richard T. Stouffer
Attorney, Agent, or Firm—Laney, Dougherty, Hessin & Beavers

[57] ABSTRACT

A patient restraint apparatus allowing relative freedom of movement for the patient. The restraint apparatus includes a bag portion made primarily of lightweight mesh material having a lockably closeable zippered positioning opening at one end thereof and an adjustable, lockable neck opening at another end thereof. Lockably closeable zipper access opening are provided in the front of the bag. A plurality of attaching straps are connected to the bag and disposed transversely with respect thereto. The straps are connected to one side of the bag at a location transversely spaced from longitudinal edges of the bag. In one operating position, the straps are positioned below the bag on a sleeping surface, and the straps are adapted for attachment to an object, such as a bed member, below the sleeping surface. The longitudinal edges of the bag are not restricted by the straps, and the bag is sized to allow relative freedom of movement by a patient in the bag for normal movement, such as during sleeping periods. In a second operating position, the straps are used to variably restrict the patient's movement. A plurality of fabric handles are attached to the edges of the bag to facilitate moving the patient while restrained therein. A supporting object, such as a pole, may be passed through the handles to adapt the apparatus as a stretcher.

15 Claims, 3 Drawing Sheets

PATIENT RESTRAINT APPARATUS

BACKGROUND OF THE INVENTION

1. Field of the Invention

The apparatus of the present invention relates to devices for restraining patients, and more particularly, to a patient restraint apparatus which may be positioned to allow relative freedom of movement for the patient.

2. Description of the Prior Art

It is well known that it is frequently necessary to physically restrain medical patients, and particularly patients suffering from some sort of mental disorder. A variety of apparatus have been developed to accomplish the purpose of restraining a patient so that the patient will not injure himself or others. Such apparatus should also allow medical personnel to treat the patient. The familiar straitjacket is an example of such apparatus. A restraining apparatus which restrains the entire body of the patient is disclosed in U.S. Pat. No. 2,948,278 to Topa.

Restraining apparatus have also been devised to restrain a patient to a hospital bed. U.S. Pat. No. 892,047 to Halterman discloses a hospital bed sheet which can be tied to the bed. The sheet has a pair of leaves which are folded over the patient and tied together, loosely or tightly as circumstances may require. The longitudinal sides of the leaves are fixed to the sheet. While the apparatus of Halterman may be somewhat looser than typical restraining devices, the patient must still be fairly tightly restrained so that he cannot work his way out of the enclosure.

There is a need, which has not been met by the prior art, for a patient restraining apparatus which allows relatively great freedom of movement to the patient. Freedom of movement is particularly important when a patient is sleeping, because people ordinarily move a great deal when they are asleep. Physically restricting movement of a patient in such circumstances can disrupt sleep and add to present disorders or cause new problems.

Also, there is a need for restraining devices for persons not under direct medical supervision, such as sleepwalkers, geriatrics, or others who might injure themselves during sleep. None of the prior art devices are adaptable to such situations.

The apparatus of the present invention meets the need of restraining a patient while allowing freedom of movement during sleeping periods and is also adapted for allowing the patient limited self car. In addition, the apparatus may also be positioned for substantially total restraint of the patient when extreme conditions require.

Basically, the prior art are all immobilizing apparatus. They are not adapted for easily moving the patient around. For example, none of the prior art, including a straitjacket, provides means for allowing the patient to walk while still connected to medical apparatus such as an I.V. Also, none of the prior restraining devices can easily be put on the patient with such medical apparatus already in place, as can be done with the present invention.

SUMMARY OF THE INVENTION

The patient restraining apparatus of the present invention comprises body enclosure means for substantially enclosing a body of a patient while having a first operating position in which the patient has freedom of movement within the body enclosure means, and attachment means for attaching the body enclosure means to an object such as a bed member or a chair. The apparatus also has a second operating position in which the body of the patient may be at least partially restrained by the attachment means while enclosed by the body enclosure means.

The body enclosure means is best characterized by a bag portion defining a central cavity therein for receiving and enclosing the patient's body. A lockably adjustable neck opening in the bag portion provides means for allowing extension of the patient's head from the bag when desired.

A positioning opening into the central cavity provides means of access so that the patient's body may be positioned in the central cavity of the bag. The positioning opening also provides adjustable means for allowing extension of the lower portion of the patient's body from the bag if desired. In the preferred embodiment, the positioning opening is lockably closeable.

The apparatus further comprises access means on the body enclosure means for providing access to the patient's body while still maintaining substantial enclosure thereof. In the preferred embodiment, the access means is characterized by a lockably closeable opening in a side of the bag. Such opening may be located to allow extension of the patient's arms and legs as desired. Also, medical devices such as I.V.'s and related tubing can be passed through the access means.

Lock means are utilized for locking all of the openings and for preventing the patient from self-release from the body enclosure means.

The attachment means is preferably characterized by a plurality of attaching strips which are attached to one side of the bag portion. Each of the straps has at least one free end for attachment to a fixed object. The straps are transversely oriented with respect to the bag portion and have an attachment location between longitudinal edges of the bag portion and spaced therefrom.

The attachment means further includes a male buckle portion attached to the strap, and the male buckle portion is engageable with a female buckle portion which is attached to a separate strap connected to any desired object, such as a bed member. The buckles preferably are of a quick-disconnect type.

In the first operating position on a sleeping surface, the first side, to which the straps are attached, is a lowermost side oft he bag and is in contact with the sleeping surface. In this orientation, the straps are below the bag portion. The bag is sized for allowing relative freedom of movement by the patient within the bag, such that the patient may move as necessary for normal sleep behavior when the apparatus is in this first operating position, even though the straps are attached to a bed member below the sleeping surface.

When necessary, the patient may be substantially totally restrained in the bag by reversing the bag to a second operating position in which the first side, and the straps attached thereto, are above the bag. In this way, the straps may then be utilized to rigidly restrain the patient.

It is an important object of the invention to provide a patient restraining apparatus which may be used to partially restrain a patient while still allowing some freedom of movement for the patient.

It is another object of the invention to provide an apparatus for restraining a patient to a sleeping surface while allowing normal sleep movement of the patient.

It is a further object to provide a patient restraint device which can be used to allow relative freedom of movement to the patient or which alternatively can be used to rigidly restrain the patient.

It is still another object of the invention to provide a patient restraining apparatus having means for access to the patient by medical personnel and for allowing limited self care by the patient.

Additional objects and advantages of the invention will become apparent as the following detailed description of the preferred embodiment is read in conjunction with the accompanying drawings which illustrate such preferred embodiment.

BRIEF DESCRIPTION OF THE DRAWINGS

FIG. 3 is a side elevation of a male buckle portion of the restraining system used in the apparatus.

FIG. 5 is a detail view of the locking system usable for openings into the apparatus.

DESCRIPTION OF THE PREFERRED EMBODIMENT

Figure 1:
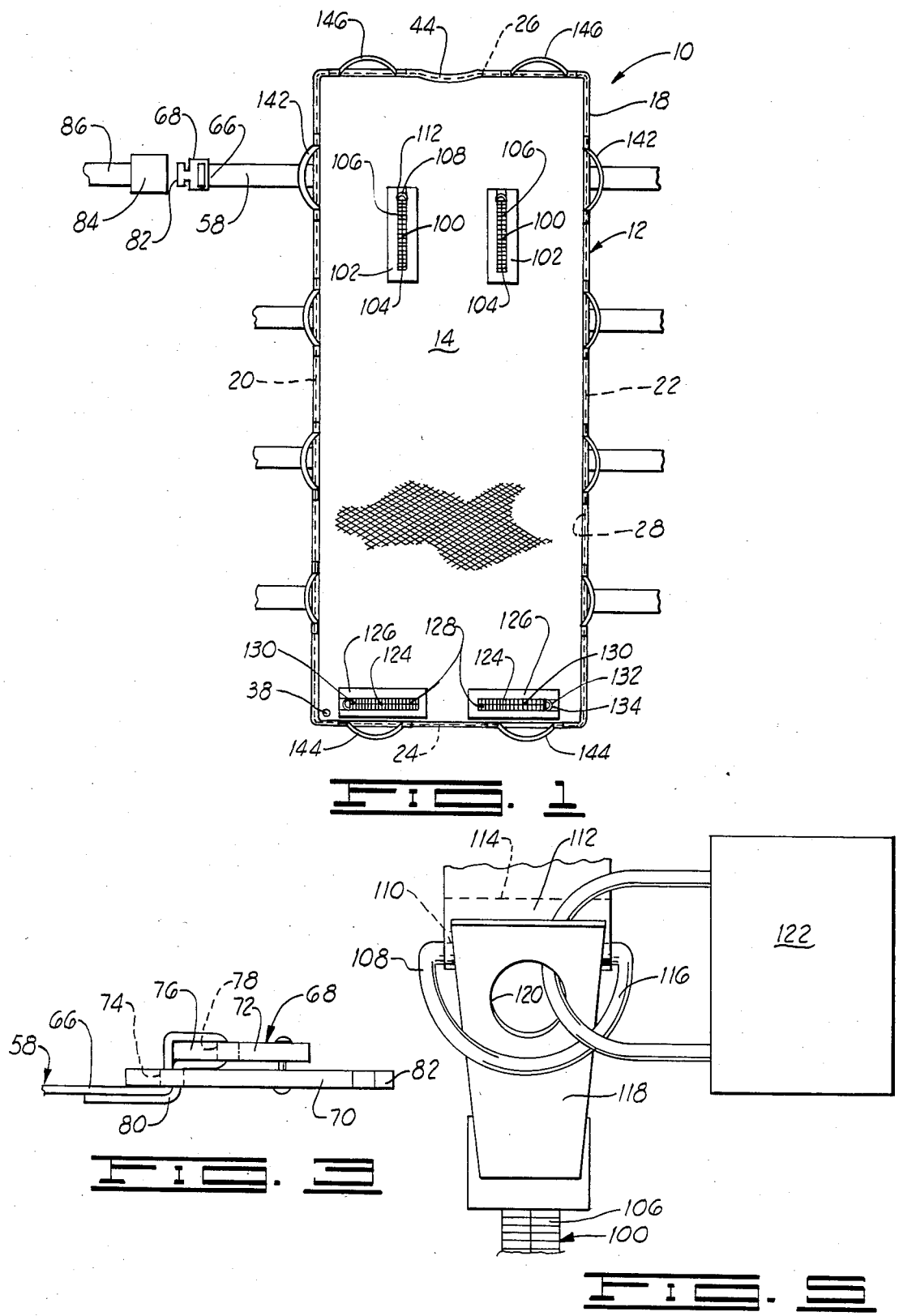
FIG. 1 shows a front or top view of the patient restraining apparatus of the present invention.
Figure 2:
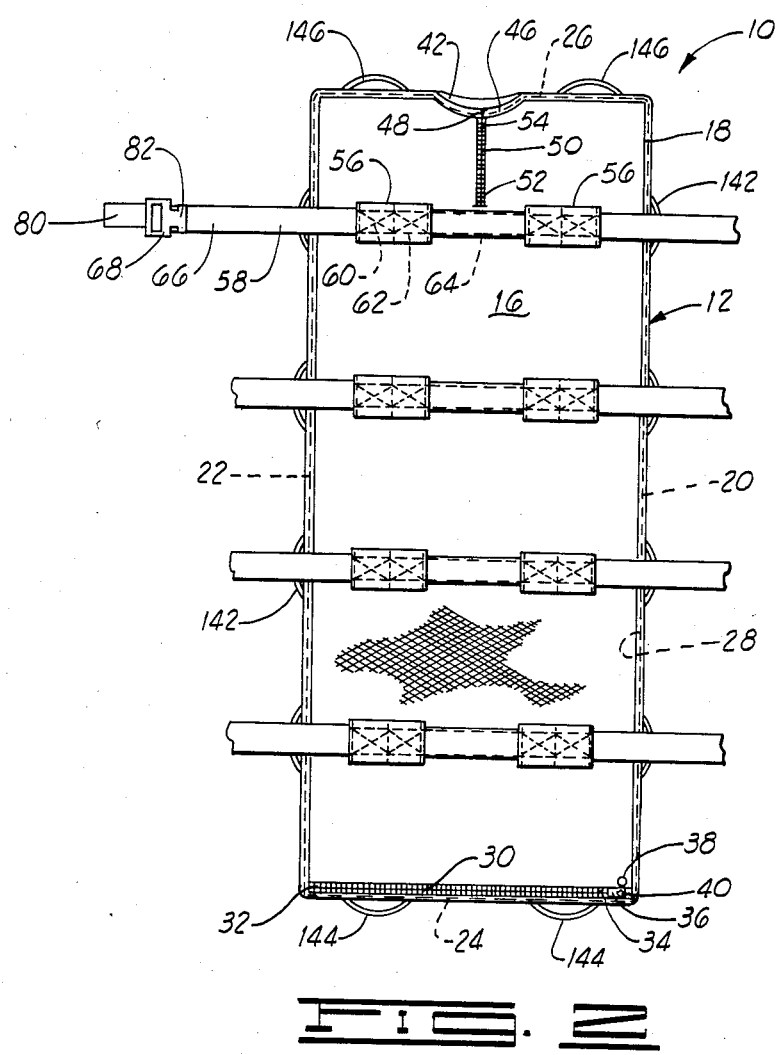
FIG. 2 is a back or bottom view of the apparatus.

Referring now to the drawings, and more particularly to FIGS. 1 and 2, the patient restraint apparatus of the present invention is shown and generally designated by the numeral 10.

A major component of apparatus 10 is an elongated bag portion 12 having a front panel 14 attached to a back panel 16 by a binding 18 sewn along longitudinal edges 20 and 22, transverse lower edge 24, and partially along transverse upper edge 26. Preferably, front panel 14 and rear panel 16 are made of a lightweight mesh material, such as non-abrasive, flame-retardant, nylon netting. This type of material also provides substantial visibility of a patient in bag portion 12. Normally, bag portion 12 is made from a single piece of material, folded along one of longitudinal edges 20 or 22. However, front panel 14 and rear panel 16 could also be made from two separate pieces of material. Because front panels 14 and 16 are joined only along their respective edges, it will be obvious that bag 12 thus defines a central cavity 28 therein.

Adjacent lower edge 24 is a zippered positioning opening 30 which opens into central cavity 28 and is used to position a patient in bag portion 12. Positioning opening 30 may also be used to allow a lower portion of the patient's body to be extended from bag portion 12. Positioning opening 30 has a fixed end 32 and an opposite end 34. When the zipper of positioning opening 30 is closed, handle 36 of the zipper is positioned at end 34. A hole 38, preferably formed by a metal eye, is dispersed through both front panel 14 and rear panel 16 adjacent end 34 of positioning opening 30. Handle 36 defines a hole 40 therethrough, and by passing a padlock or similar means known in the art (not shown) through both holes 38 and 40, it will be seen that means are provided for lockably closing zippered positioning opening 30.

Bag 12 also defines a neck opening 42 therein in communication with central cavity 28 and through which the patient's head and neck maybe extended. Neck opening 42 is disposed at an intermediate location along upper edge 26 of bag 12 and is reinforced by a front neck binding 44 and a rear neck binding 46. Neck binding 46 is longitudinally split at an intermediate point 48 thereof. Both front and rear neck bindings 44 and 46 are padded to relieve pressure on the patient's neck.

Neck opening 42 also includes a zippered portion 50 having a lower fixed end 52 and an upper end 54 adjacent rear neck binding 46. Zippered portion 50 is preferably of the self-locking type known in the art. Thus, neck opening 42 is lockably closeable although it is not always necessary to lock the opening. Further, zippered portion 50 is adapted to be lockable at any intermediate position between lower fixed end 52 and upper end 54 to provide for adjustable sizing of neck opening 42 as desired.

Referring to the back view in FIG. 2, a plurality of reinforcement pads 56 is sewn to back panel 16. Each pad 56 is transversely spaced from longitudinal sides 20 and 22 of bag 12. Also, each pad 56 has a corresponding pad 56 transversely aligned therewith, and, in the embodiment shown in FIG. 2, four such pairs of pads 56 are illustrated. The preferred material for pads 56 is vinyl-covered nylon, although any suitably strong material would be adequate.

A transversely oriented attaching strap 58, preferably made of strong nylon webbing, is securely sewn to each pair of pads 56 by stitching in an X pattern 60 or other suitably strong sewing technique. Straps 58 are also sewn with a transverse stitch 62 to pads 56 and bag 12. A transverse stitch 64 is used to sew each strap 58 to bag 12 between pads 56. Straps 58 are not attached to bag 12 at any point transversely outwardly of pads 56. In other words, each strap 58 has an attachment location on bag 12 between longitudinal edges 20 and 22 and transversely spaced therefrom. Strap 58 thus has a pair of ends 66 extending transversely outwardly from bag 12.

The preferred longitudinal spacing of straps 58 and corresponding pads 56 is such that they are located approximately adjacent the shoulders, waist, hips and knees of a patient positioned in bag portion 12. The quantity and spacing, however, are not limited to such an arrangement.

Adjustably connected to each end 66 of strap 58 is a male buckle portion 68, as shown in FIG. 3. Male buckle portion 68 includes a latch plate 70 and a gripping plate 72. End 66 of belt 58 is passed through a slot 74 in latch plate 70, over end 76 of gripping plate 72 and through a slot 78 in the gripping plate. End 66 of strap 58 then is passed back under end 76 of gripping plate 72 and through slot 74 again. Thus, a free end 80 extends from male buckle portion 68.

When strap 58 is slack, the length of free end 80, and thus the relationship between male buckle portion 68 and longitudinal sides 20 and 22 of bag 12 may be adjusted. When tension is applied on strap 58 by pulling on male buckle portion 68, the two portions of strap 58 which pass through slot 74 are frictionally gripped together. Such an arrangement is known in the art, and was formally used on automobile seat belt buckles.

Referring to FIGS. 1–3, latch plate 70 of male buckle portion 68 has an engaging end 82 adapted for releasable engagement to a quick-disconnect female buckle portion 84 in a manner known in the art. As shown in FIG. 2, male buckle portion 68 is folded over so that engaging end 82 thereof is pointed toward bag 12. Free end 80 of strap 58 is shown extending transversely away from male buckle portion 68. In this position, the length of free end 80 is easily adjusted. As shown in FIG. 1, engaging end is ready to engage female buckle portion 84.

Figure 4:
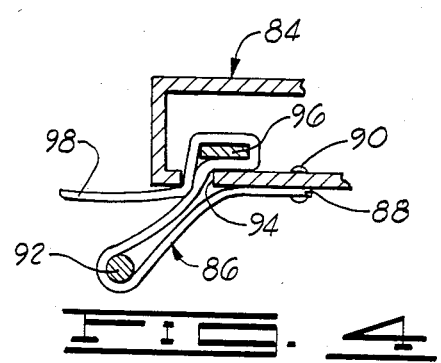
FIG. 4 is a cross-sectional view of a female buckle attachable to the male buckle shown in FIG. 3.

Female buckle portion 84 has another strap 86 connected thereto in a manner best illustrated in FIG. 4. Strap 86 has a first end 88 fixedly attached to female buckle portion 84 by fastening means such as rivet 90. Originally, the remainder of strap 86 is free so that it can be wrapped around any desired object 92, such as a bed member, in a manner hereinafter described in more detail. After being placed around object 92, strap 86 is then passed through a slot 93, in female buckle portion 84, around a bar 96, and back through slot 94 so that a free end 98 of strap 86 extends from the female buckle portion.

When strap 86 is slack, the length of free end 98 thereof, and thus the relationship between female buckle portion 84 and object 92, may be adjusted in a manner similar to that for male buckle portion 68. When tension is applied on strap 86 by female buckle portion 84, the strap is tightly retained in the buckle.

Referring again to FIG. 1, a pair of zippered patient access openings 100 are shown with a reinforcement pad 102 therearound. Each zippered access opening has a fixed end 104 and an opposite end 106. Access openings 100 are adapted to be adjacent a patient's arms, and allow medical devices such as I.V.'s to be positioned therethrough. Medical personnel also have access to the patient for carrying such medical procedures as injections and the like.

In FIG. 5, an enlarged view of end 106 of an access opening 100 is shown. Adjacent end 106 is a substantially D-shaped, metal ring 108 which has a straight portion1 110 enclosed in a fabric loop 112. Fabric loop 112 is attached to pad 102 by stitching 114. Ring 108 also has a curvilinear portion 116 adapted to receive handle 118 of zippered opening 100. Handle 118 defines a hole 120 therethrough which may be engaged by locking means such as a padlock 122. When padlock 122 is so placed, zippered opening cannot be opened, and is thus lockably closable. When lock 122 is removed, zippered opening 100 may be opened to provide the mentioned access to the patient by medical personnel. Also, access openings 100 allow the patient to have some free arm movement for self care when appropriate.

FIG. 1 also shows a second pair of access openings 124 having a reinforcement pad 126 therearound. As illustrated, access openings 124 are substantially parallel to transverse lower edge 24 of bag 12. However, access openings 124 could also be positioned perpendicular to lower edge 24. Access openings 124 are of substantially identical construction to access openings 100. Each access opening 124 is zippered and has a fixed end 128 and an opposite end 130. Adjacent end 130 is substantially D-shaped, metal ring 132 enclosed in a fabric loop 134. Openings 124 are adapted to be lockably closeable in a manner identical to access openings 100, as illustrated in FIG. 5. Openings 124 are adapted to be adjacent the legs of the patient, so that a portion, or all, of the legs may be extended therethrough as desired.

Figure 6:
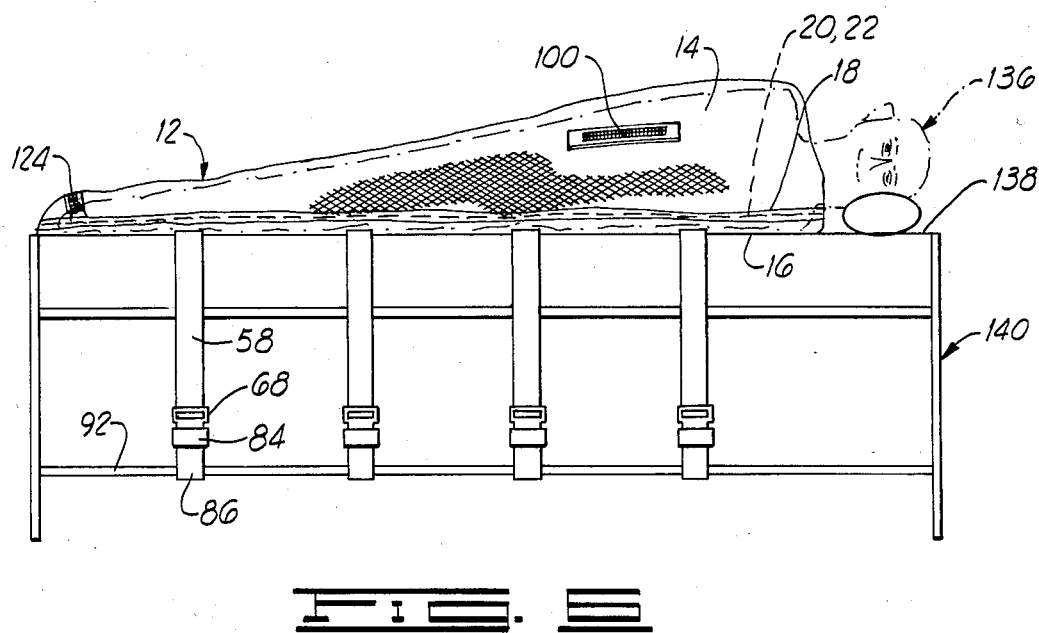
FIG. 6 illustrates a patient enclosed in the apparatus and positioned on a bed with the apparatus attached to lower bed members.

FIG. 6 illustrates the apparatus in use for restraining a patient 136 to a sleeping surface 138, such as the mattress of a bed 140. Straps 58 extend outwardly along the side of bed 140 such that male buckle portion 68 is attached to female buckle portion 84 at a point below sleeping surface 138. Strap 86 is wrapped around object 92, which in this case is a horizontal bed member below sleeping surface 138.

In the operating position shown in FIG. 6, back panel 16 is the lowermost side of bag 12 and is in substantial contact with sleeping surface 138. In other words, straps 58, attached to bag 12, are below the bag. Bag 12 is sized such that relative freedom of movement is allowed to patient 136 within the bag. Patient 136 is able to move, to turn and to maintain a comfortable posture. While restrained, the patient is not immobilized, as with prior devices. Because straps 58 are attached to panel 16 transversely spaced inwardly from longitudinal edges 20 and 22, this freedom of movement is enhanced. In other words, longitudinal edges 20 and 22 are not rigidly held to sleeping surface 138.

The freedom of movement allowed by the apparatus in the position shown in FIG. 6 is extremely important for normal sleeping. All people move a great deal during their sleep, and if they are rigidly constrained, they will be frequently awakened, and thus a normal sleep pattern is not possible. In addition to tiring the patient, lack of proper sleep can cause severe mental disorientation.

Further, when apparatus 10 is used in the position shown in FIG. 6, the patient has reduced feelings of being confined as compared to prior devices. This is a critical factor in many psychiatric situations.

By positioning front panel 14 as a lowermost side of bag 12, and thereby in contact with sleeping surface 138, it will be clear that straps 58 pass over patient 136 because panel 16 is above the patient. In this inverted, second operating position, straps 58 can be used to variably restrict movement of the patient in the extreme situations where it is necessary to do so. Any degree of restriction is possible by adjusting straps 58 and 86, including immobilization.

In addition to using the apparatus to hold a patient on sleeping surface 138, it will be clear to those skilled in the art, that straps 58 could be used in a similar manner to restrain a patient to a chair. Again, in the first operating position, the patient has relatively greater freedom of movement than with prior apparatus. In fact, many of the prior apparatus cannot be adapted for use with a chain in any case.

Other advantages of apparatus 10 which are not available in the prior art devices include the ability to extend the patient's legs through openings 124 so that the patient may walk around. By lockably closing openings 124 adjacent the patient's knee, the patient is prevented from running. In other words, the patient may be easily moved without being released from apparatus 10.

Another advantage to the apparatus is that because of the mesh material, the patient is completely visible to medical personnel, and the patient may be bathed in bag 12.

Apparatus 10 is useful not only when medical personnel must be present, but also for other less closely supervised situations. Examples include use of the apparatus by sleepwalkers, geriatrics, and persons suffering from disabilities which increase the likelihood of injury during sleep.

It will be obvious that by varying the tightness of straps 58 in the operating position shown in FIG. 6, apparatus 10 can even be adapted so that a person may sit up in bed, while still being relatively restrained to the sleeping surface thereof so that the person cannot roll out of bed during sleep. In all of these situations, the apparatus provides for normal sleeping behavior.

Figure 7:
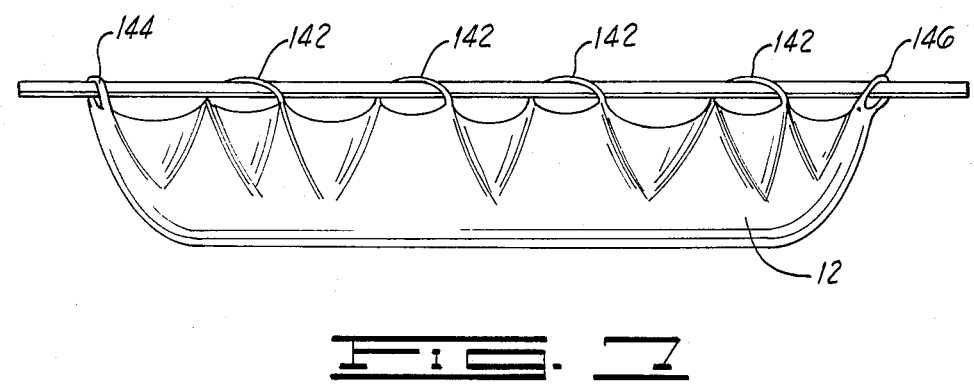
FIG. 7 illustrates use of the apparatus as a stretcher.

Referring again to FIGS. 1 and 2, and also to FIG. 7, a plurality of fabric handles 142 are attached to binding 18 along longitudinal edges 20 and 22 of bag 12. Preferably, the fabric is doubled nylon webbing. Each handle 142 is adjacent a strap 58. A pair of handles 144 are also attached to lower end 24 of bag 12, adjacent zippered positioning opening 30. Similarly, a pair of handles 146 are attached to upper end 26 of bag 12 on opposite sides of neck opening 42.

Handles 142, 144 and 146 may be used as necessary to manually move bag 12 with a patient enclosed therein. Further, by passing support means, such as a pole 148, through handles 142 on each longitudinal side of bag 12, and also through corresponding lower handle 144 and upper handle 146, on both sides of the apparatus, a stretcher is quickly provided for transport of the patient. In this case, it is best to pull neck opening 42 up over the head of the patient so the patient is totally enclosed. Thus, the apparatus has the advantage over prior arrangements where the patient would have to be released from the restraining apparatus and then again restrained to the stretcher. Handles 142, 144 and 146 provide means for transporting the patient while restrained.

Whenever a patient is in bag 12 of apparatus 10, the patient is clearly restrained therein. If the patient tries to escape, it is "like punching your way out of a paper bag". Pushing on one side results in the other side pulling against the patient. The patient can get no leverage with which to tear his way out. Clinical tests have shown the apparatus to be extremely effective.

It can be seen, therefore, that the patient restraining apparatus of the present invention is well adapted to carry out the ends and advantages mentioned, as well as those inherent therein. While a presently preferred embodiment of the apparatus has been shown for the purposes of this disclosure, numerous changes in the construction and arrangement of the parts may be made by those skilled in the art. All such changes are encompassed within the scope and spirit of this invention as defined by the appended claims.

What is claimed is:

1. An apparatus for restraining a patient, said apparatus comprising:
    body enclosure means with longitudinal and upper and lower edges for extending around and substantially enclosing a body of said patient and having a position in which said patient has freedom of movement within said body enclosure means;
    access means on said body enclosure means for providing access to said body of said patient while maintaining substantial enclosure thereof, said body enclosure means and said access means being adaptable for preventing opening of said access means by said patient;
    attachment means, connected to said body enclosure means at a location transversely spaced from the longitudinal edges of said body enclosure means, for attaching said body enclosure means to an object without said attachment means restricting movement of said body of said patient within said body enclosure means; and
    a plurality of elongated handles, each of said handles being attached at opposite ends thereof to one of the edges of said body enclosure means.

2. The apparatus of claim 1 wherein said body enclosure means includes means for allowing extension of said patient's head from said body enclosure means.

3. The apparatus of claim 1 further comprising means for allowing extension of a lower portion of said patient's body from said body enclosure means.

4. The apparatus of claim 1 wherein:
    said body enclosure means is characterized by a body enclosing bag with a closeable opening for receiving said patient's body; and
    said attachment means is characterized by a strap having:
        a portion attached to a side of said bag; and
        an end spaced from said bag and adapted for attaching to said object.

5. The apparatus of claim 1 further comprising lock means for locking said access means.

6. A patient restraint apparatus comprising:
    a bag portion defining a central cavity therein for receiving and enclosing a body of said patient while allowing freedom of movement and rotation of said body within said bag portion, said bag portion having a pair of sides and defining a neck opening into said central cavity, said bag portion further defining an access opening into said central cavity such that access is available to said body of said patient when said body is positioned in said central cavity, said bag portion being adapted for preventing access to said opening by said patient when said body is in said central cavity;
    a plurality of attaching straps connected to one of said sides of said bag portion and extending transversely away from said bag portion, each of said straps having at least one end adapted for attachment to a fixed object; and
    a plurality of elongated handles attached to said bag portion, each of said handles being attached at opposite ends thereof to an edge of said bag portion.

7. The apparatus of claim 6 wherein said access opening is lockably closeable.

8. The apparatus of claim 6 wherein said bag portions further defines a lockably closeable positioning opening through which said patient is receivable for enclosure in said central opening of said bag portion.

9. The apparatus of claim 6 wherein said bag portion comprises a mesh material.

10. An apparatus for restraining a patient adjacent a sleeping surface, said apparatus comprising:
    an elongated bag defining a body positioning opening thereinto for receiving a body of said patient, said body positioning opening being closeable for enclosing said body in said bag such that access to said body positioning opening by said patient is prevented, and further defining a neck opening thereinto and through which said patient's neck and head may be extended, said bag having a first side and a second side attached to said first side along adjacent edges of said sides;
    a plurality of transversely oriented straps fixedly attached to said first side of said bag and having an attachment location spaced from longitudinal edges thereof, each of said straps having a pair of opposite ends extending transversely from said attachment location and being adapted for releasable attachment to an object below said sleeping surface, and a plurality of elongated flexible handles, each of said handles having opposite ends attached to one of the edges of said bag, said handles being adaptable for hand engagement by medical personnel and further being adapted for receiving support means therethrough; said apparatus having:

a first operating position in which said first side is a lowermost side of said bag is adapted to be in contact with said sleeping surface such that said straps are below said bag and said straps do not restrict movement of said patient, said bag being sized for allowing relative freedom of movement and rotation by said patient within said bag for normal sleeping positions; and a second operating position in which said first side is an uppermost side of said bag such that said straps are disposed above said bag for variably restricting movement of said patient.

11. The apparatus of claim 10 wherein said second side of said bag defines at least one closeable access opening therethrough for providing access to said patient in said bag by medical personnel and for limiting access outside of said bag by said patient.

12. The apparatus of claim 10 wherein said bag is made of a mesh material.

13. The apparatus of claim 10 wherein:
said sleeping surface to which said apparatus is adapted to be in contact is a bed mattress; and
said object to which said straps are adapted to be releasably attached is a bed frame member.

14. The apparatus of claim 10 wherein said neck opening is lockably adjustable in size.

15. The apparatus of claim 10 wherein said body positioning opening is lockable.

* * * * *

UNITED STATES PATENT AND TRADEMARK OFFICE
CERTIFICATE OF CORRECTION

PATENT NO. : 4,742,821

DATED : May 10, 1988

INVENTOR(S) : Gerald D. Wootan

It is certified that error appears in the above-identified patent and that said Letters Patent are hereby corrected as shown below:   Title page:

Abstract, line 7, delete "zipper" and insert --zippered-- therefor; line 7, delete "opening" and insert --openings-- therefor.

Column 1, line 50, delete "car" and insert --care-- therefor; line 65, delete "restraining" and insert --restraint-- therefor.

Column 2, line 50, delete "oft he" and insert --of the-- therefor.

Column 3, line 6, delete "alternatively" and insert --alternately-- therefor; line 9, delete "restraining" and insert --restraint-- therefor; lines 19-20, delete "restraining" and insert --restraint-- therefor; line 23, delete "restraining" and insert --restraint-- therefor; lines 63-64, delete "dispersed" and insert --disposed-- therefor.

Column 4, line 5, delete "maybe" and insert --may be-- therefor; line 16, after "closeable" and before "although", insert --,--.

Column 5, line 17, delete "93" and insert --94-- therefor; line 39, delete "portionl" and insert --portion-- therefor; line 59, after "is" and before "substan-", insert --a--; line 68, delete "outwardly" and insert --downwardly-- therefor.

Column 6, line 47, delete "chain" and insert --chair-- therefor.

Column 7, line 26, delete "restraining" and insert --restraint-- therefor.

UNITED STATES PATENT AND TRADEMARK OFFICE
CERTIFICATE OF CORRECTION

PATENT NO. : 4,742,821

DATED : May 10, 1988

INVENTOR(S) : Gerald D. Wootan

It is certified that error appears in the above-identified patent and that said Letters Patent are hereby corrected as shown below:

Claim 8, line 1, delete "portions" and insert --portion-- therefor.

Signed and Sealed this

Twentieth Day of September, 1988

Attest:

DONALD J. QUIGG

Attesting Officer

Commissioner of Patents and Trademarks